(12) United States Patent
Kals et al.

(10) Patent No.: US 8,892,212 B2
(45) Date of Patent: Nov. 18, 2014

(54) FAST FITTING OF COCHLEAR IMPLANTS

(71) Applicant: MED-EL Elektromedizinische Geraete GmbH, Innsbruck (AT)

(72) Inventors: Mathias Kals, Innsbruck (AT); Marek Polak, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 186 days.

(21) Appl. No.: 13/685,862

(22) Filed: Nov. 27, 2012

(65) Prior Publication Data

US 2013/0138180 A1    May 30, 2013

Related U.S. Application Data

(60) Provisional application No. 61/563,890, filed on Nov. 28, 2011.

(51) Int. Cl.
*A61N 1/36* (2006.01)

(52) U.S. Cl.
CPC ................................ *A61N 1/36032* (2013.01)
USPC ............................................. 607/57; 607/59

(58) Field of Classification Search
None
See application file for complete search history.

(56) References Cited

U.S. PATENT DOCUMENTS

| | | | |
|---|---|---|---|
| 8,401,656 B2 * | 3/2013 | Smoorenburg | 607/57 |
| 8,571,675 B2 * | 10/2013 | Dijk | 607/57 |
| 2006/0100672 A1 * | 5/2006 | Litvak | 607/57 |
| 2006/0235332 A1 * | 10/2006 | Smoorenburg | 600/559 |
| 2007/0179565 A1 * | 8/2007 | Overstreet et al. | 607/57 |

* cited by examiner

*Primary Examiner* — Kennedy Schaetzle
(74) *Attorney, Agent, or Firm* — Sunstein Kann Murphy & Timbers LLP

(57) ABSTRACT

Approaches are described for fitting an implanted cochlear implant having electrode array contacts to the implanted patient. A normal electrode stimulation arrangement is used to deliver electrode stimulation signals to the active electrode channel electrode contacts at an initial common charge level. The common charge level is increased until a desired common percept criteria is met to establish a common baseline charge level for the stimulation electrode contacts. For each individual electrode contact, a fitting stimulation signal is delivered to the electrode starting from the common baseline charge level and the charge level is increased until an individual electrode percept criteria is met.

24 Claims, 3 Drawing Sheets

FAST FITTING OF COCHLEAR IMPLANTS

This application claims priority from U.S. Provisional Patent Application 61/563,890, filed Nov. 28, 2011, which is incorporated herein by reference.

TECHNICAL FIELD

The present invention relates to medical implants, and more specifically to fit customization in audio prosthesis systems such as cochlear implant systems.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant processor 108. Besides receiving the processed audio information, the implant processor 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrode contacts on its surface that provide selective stimulation of the cochlea 104.

Cochlear implant systems employ stimulation strategies that provide high-rate pulsatile stimuli in multi-channel electrode arrays. One specific example is the "Continuous Interleaved Sampling (CIS)"—strategy, as described by Wilson et al., *Better Speech Recognition With Cochlear Implants*, Nature, vol. 352:236-238 (1991), which is incorporated herein by reference. For CIS, symmetrical biphasic current pulses are used, which are strictly non-overlapping in time. The rate per channel typically is higher than 800 pulses/sec. Other stimulation strategies may be based on simultaneous activation of electrode currents. These approaches have proven to be successful in giving high levels of speech recognition.

For an audio prosthesis such as a cochlear implant to work correctly, some patient-specific operating parameters need to be determined in a fit adjustment procedure where the type and number of operating parameters are device dependent and stimulation strategy dependent. Possible patient-specific operating parameters for a cochlear implant include:

$THR_1$ (lower detection threshold of stimulation amplitude) for Electrode 1
$MCL_1$ (most comfortable loudness) for Electrode 1
Phase Duration for Electrode 1
$THR_2$ for Electrode 2
$MCL_2$ for Electrode 2
Phase Duration for Electrode 2
. . .
Pulse Rate
Number of fine structure channels
Compression
Parameters of frequency→electrode mapping
Parameters describing the electrical field distribution One approach for an objective measurement of MCLs and THLs is based on the measurement of the eCAPs (Electrically Evoked Compound Action Potentials), as described by Gantz et al., *Intraoperative Measures of Electrically Evoked Auditory Nerve Compound Action Potentials*, American Journal of Otology 15 (2):137-144 (1994), which is incorporated herein by reference. In this approach, a recording electrode in the scala tympani of the inner ear is used. The overall response of the auditory nerve to an electrical stimulus is measured very close to the position of the nerve excitation. This neural response is caused by the super-position of single neural responses at the outside of the axon membranes. The amplitude of the EAP at the measurement position is between 10 µV and 1800 µV.

One common method for fit adjustment is to behaviorally find the threshold (THR) and most comfortable loudness (MCL) value for each separate electrode contact. For this, the stimulation charge on a selected electrode channel is usually increased in steps from zero until the THR or MCL level is reached in a behavioral procedure (e.g. method of adjustments) or an objective procedure (i.e. eSRT). Typically, for this procedure constant amplitude stimulation bursts with durations of 10-1000 msec duration are utilized. See for example, Rätz, *Fitting Guide for First Fitting with MAESTRO 2.0*, MED-EL, Fürstenweg 77a, 6020 Innsbruck, 1.0 Edition, 2007. AW 5420 Rev. 1.0 (English_EU); incorporated herein by reference. Other alternatives/extensions are sometimes used with a reduced set of operating parameters; e.g. as suggested by Smoorenburg, *Cochlear Implant Ear Marks*, University Medical Centre Utrecht, 2006; U.S. Patent Application 20060235332; which are incorporated herein by reference. Typically each electrode channel is fitted separately without using the information from already fitted electrode channels. The stimulation charge on a given electrode contact typically is increased in steps from zero until the MCL (most comfortable loudness) is reached.

Several approaches currently are used to accelerate the fitting process. One approach is to use a flat map, i.e. use the same MCL or THR value on all electrode channels so that only one electrode channel needs to be fitted. But this approach allows no conclusion to be drawn about the perceptive status (high or less sensitive) of fitted electrode channel and consequently the resulting map can be in much too loud or too soft for some electrode channels. Another approach is to increase electrode stimulation charge during fitting on N adjacent electrodes simultaneously from zero onwards and thereby so to speak fit N adjacent electrodes simultaneously. These and similar approaches do save time, however, they have the disadvantage of not taking into account electrode specific particularities, like, e.g., a certain electrodes having a considerably different MCL value from another electrodes. A third used approach for example is to not start from zero when fitting an electrode but from a certain fixed value. This approach however has the disadvantage of the fixed starting values possibly being too high with respect on MCL on one electrode and possibly being much too low with respect to MCL on another electrode. In other words, the risk of over-stimulating the patient exists, while there is still potential of more time savings.

SUMMARY

Embodiments of the present invention are directed to fitting an implanted cochlear implant having electrode array contacts to the implanted patient. A normal electrode stimulation arrangement is used to deliver electrode stimulation signals to the electrode contacts at an initial common charge level. The common charge level is adjusted (increased or decreased) until a desired common percept criteria is met to establish a common baseline charge level for the electrode contacts. For each individual electrode contact, a fitting stimulation signal is delivered to the electrode starting from the common baseline charge level and the charge level is adjusted (increased or decreased) until an individual electrode percept criteria is met.

The electrode stimulation strategy may be a sequential or simultaneous stimulation strategy. The electrode stimulation signals may be delivered in amplitude bursts. The initial common charge level may be zero or an initial defined level greater than zero. The patient may be bilateral implant patient with left and right side electrode arrays whereby all the individual electrode contacts in both arrays are fit.

Embodiments also include a cochlear implant fitting system using a method according to any of the above, and a computer program product implemented in a computer readable storage medium for fitting an implanted electrode of a cochlear implant to an implanted patient and including program code for performing a method according to any of the above.

DETAILED DESCRIPTION

Embodiments of the present invention are directed to a method and a system which provides a starting point for the fitting of each electrode contact. In a CI (cochlear implant) fitting procedure similar charge level ranges are scanned several times to determine MCL (most comfortable loudness) and THR (threshold) levels for each electrode/channel. In this invention, a fast and efficient method to determine MCL and THR levels is presented, where any reduction of fitting steps (fitting time) is feasible. This method can be used in behavioral as well as inobjective (e.g. electrically evoked stapedius reflex threshold (eSRT)) measurements.

Figure 1:
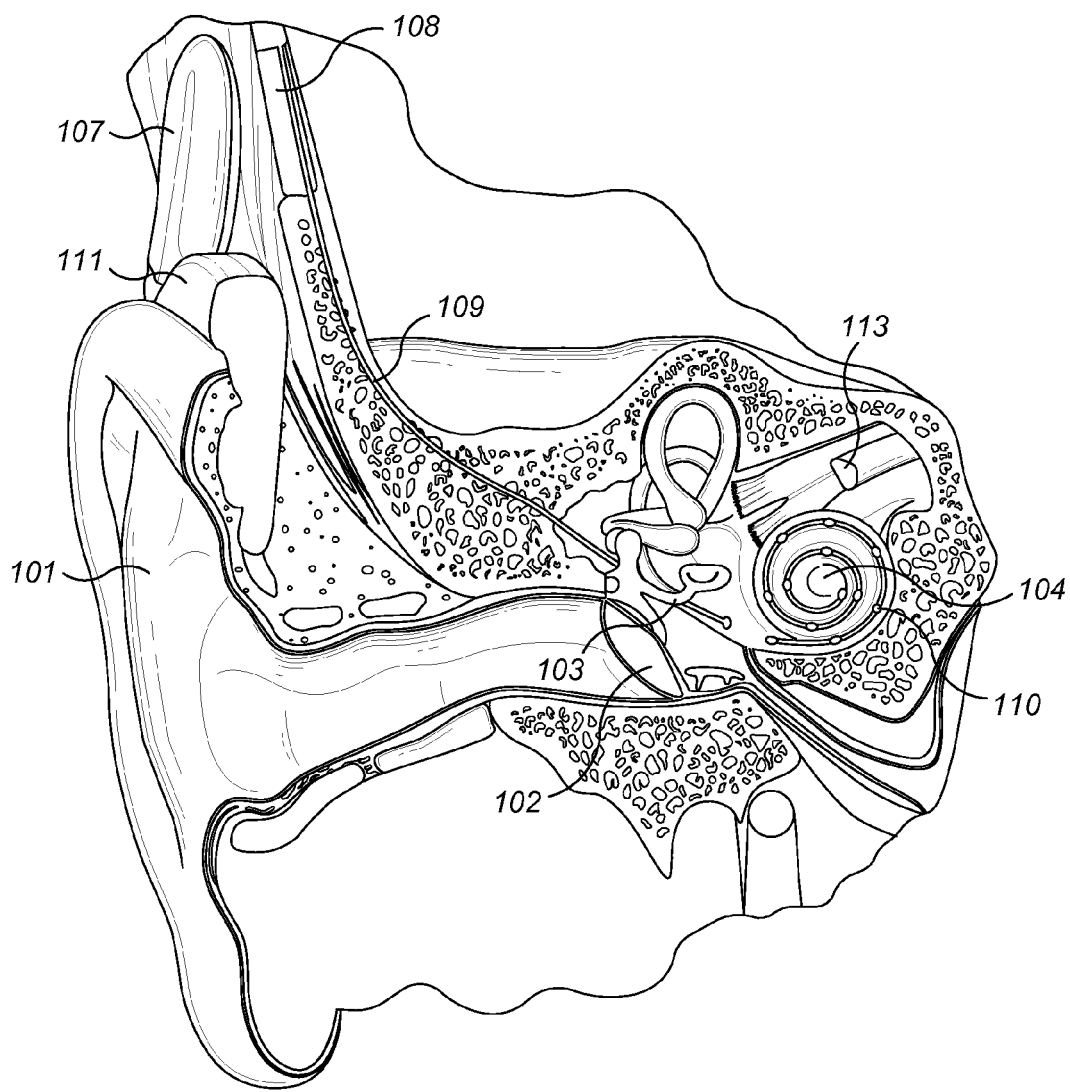
FIG. 1 shows anatomical structures in a human ear having a cochlear implant system.
Figure 2:
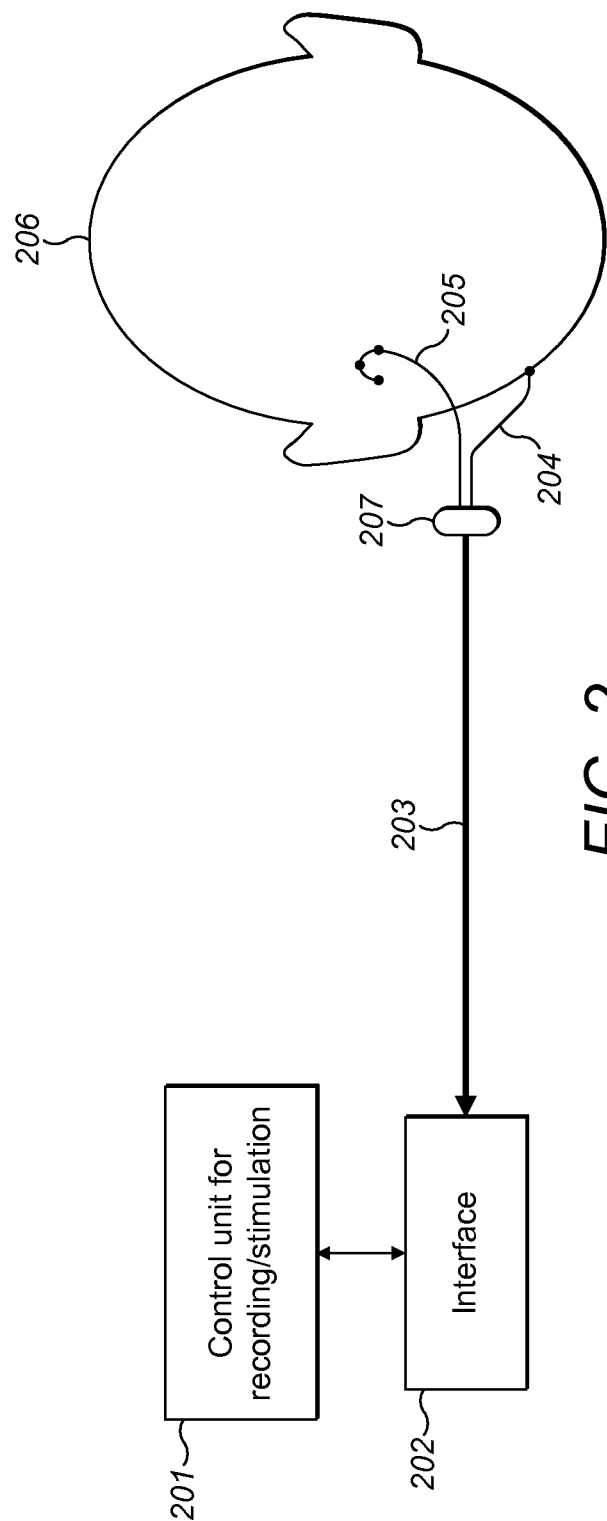
FIG. 2 shows a block diagram of a cochlear implant fitting system according to one specific embodiment of the present invention.

FIG. 2 shows a block diagram of a cochlear implant fitting system according to one specific embodiment of the present invention. Control Unit 201 for Recording and Stimulation, for example, a Med-El Maestro CI system, generates stimulation signals and analyzes response measurements. Connected to the Control Unit 201 is an Interface Box 202, for example, a Diagnostic Interface System such as the DIB II conventionally used with the Maestro CI system that formats and distributes the input and output signals between the Control Unit 201 and the system components implanted in the Patient 206. For example, as shown in FIG. 2, there may be an Interface Lead 203 connected at one end to the Interface Box 202 and at the other end having Electrode Plug 207 that then divides into a Cochlear Implant Electrode 204 and an Extra-Cochlear Ground Electrode 205. After or during delivering a stimulation pulse, a Cochlear Implant Electrode 204 may be used as a sensing element to determine current and voltage characteristics of the adjacent tissue, for example, for use measuring current spread.

Figure 3:
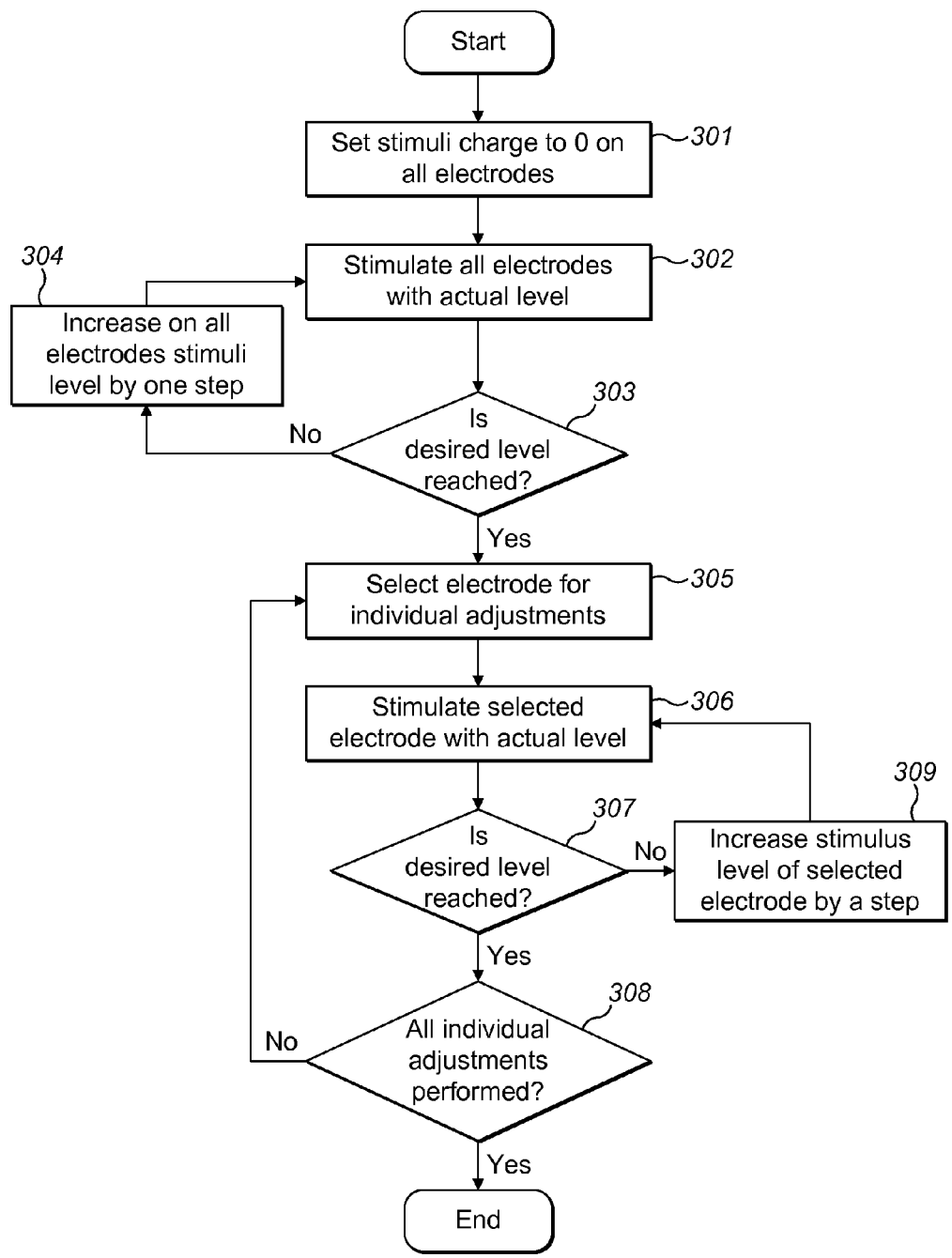
FIG. 3 shows various logical steps in performing an electrode fitting process according to one specific embodiment of the present invention.

FIG. 3 shows various logical steps in performing an electrode fitting process according to one specific embodiment of the present invention. In the first stage of the fitting, all electrode contacts share the same stimulation charge level ($Q_{common} = Q_i$, where i=the number of a given electrode contact $\{1, \ldots, N\}$. A normal operating stimulation arrangement is used for this common electrode fitting (stimulation strategy, pulse rate, channel order, frame timing, etc.) as in the final clinical configuration. When the charge-levels are adjusted, optimum electrode/channel specific pulse phase durations can be adjusted on the fly automatically accordingly to the compliance limit. For envelope-based strategies such as continuous interleaved sampling (CIS), constant-amplitude stimulation bursts may be used. Fine structure electrode channels may be different, as described in U.S. Pat. No. 6,594,525 (incorporated herein by reference), where additional temporal information may be added in stimulation patterns by specific pulse sequences. In that case, corresponding sequences with varying amplitude can be used on each fine structure electrode channel instead of constant-amplitude stimuli.

A common charge level $Q_{common}$ of the stimulus pattern initially is set at zero or some other defined non-zero initial level $Q_{start}$, step 301. For a non-zero initial charge level $Q_{start}$ a very conservative level according clinical experience is used to avoid the risk of overstimulation. The normal stimulation arrangement is used to apply the common charge level ($Q_{common}$) stimuli to the electrode contacts, step 302. The stimulation patterns may be applied continuously or in bursts (e.g. 100-500 msec duration). If a desired common percept criteria (e.g. THR, MCL or eSRT) is met at the existing common charge level, step 303, the process advances to fitting of the individual electrode contacts. Otherwise, the common charge level is adjusted (increased or decreased), step 304, and steps 302 and 303 are repeated. The common charge level fitting stage defines a common baseline charge level B for individual measurements of the electrode contacts in a second fitting stage.

Loudness summation can occur across simultaneously or consecutively activated electrode contacts (caused by temporal and spatial integration as shown by McKay C. et al., *Loudness Summation For Pulsatile Electrical Stimulation Of The Cochlea: Effects Of Rate, Electrode Separation, Level, And Mode Of Stimulation*; J Acoust Soc Am, 110(3), 2001, p. 1514-1524; incorporated herein by reference). Thus the estimated common baseline charge level B is equal or below the lowest target charge level (e.g. THR, MCL or eSTR) of individual electrode contact measurements ($B \leq \min(Q_{target, i})$). And so the common baseline charge level B is strongly related to the most sensitive electrode channel of the array and offers a safe starting point for all electrode contacts in subsequent individual electrode measurements. The interval between B and $\min(Q_{target, i})$ (safety range) can be adjusted by modifying stimulation burst duration in one or both fitting stages, since loudness percept depends on stimulation burst duration. Generally, longer stimulation bursts with identical charge per stimuli result in a louder percept. For example, a reduction of stimulation burst duration in the first common fitting stage would result in a higher baseline B and consequently smaller safety range.

For bilaterally implanted patients with an implant on both left and right sides, a similar common fitting process can be followed. In that case the obtained common baseline charge level $B_{bilateral}$ should be adjusted both for the loudness summation effect above and also for bilateral loudness summation effect (see Higson et al., *Binaural Summation Of The Acoustic Reflex*, Ear Hear, Medical Research Council Institute of Hearing Research, University of Nottingham, 1996, 17, 334-340; incorporated herein by reference). Generally, the common baseline charge level $B_{bilateral}$ obtained in a bilateral fitting procedure may therefore be smaller than the corresponding unilateral common baseline charge levels. A further refinement of common baseline charge level $B_{bilateral}$ can be performed for each side. This means that starting from common baseline charge level $B_{bilateral}$ for each side the unilateral common baseline charge level B, as described before, is adjusted.

In the second individual fitting stage, single electrode measurements for each electrode contact are performed. A given individual electrode contact i is selected, step 305, and stimulated with an electrode-specific charge level $Q_i$, step 306. The stimulation charge level $Q_i$ initially starts from the prior estimated common baseline B for all electrode contacts. If a desired individual electrode percept criteria (e.g. THR, MCL or eSRT) is met at the existing common charge level, $Q_i = Q_{target, i}$, step 307, the process returns back to fitting of the next individual electrode contact, step 305 until each individual electrode contact has been fitted, step 308. Otherwise, the stimulation charge level $Q_i$ is adjusted (increased or decreased), step 309, and steps 306 and 307 are repeated for the current electrode contact. For these individual electrode channel adjustments, the same simulation patterns can be used as in the first common fitting stage except using zero-charge stimuli $Q_j = 0$ ($j = \{1, \ldots, N\}$ and $j \neq i$) for all channels except the current electrode channel i. The use of different step sizes to optimize speed and accuracy in both fitting stages may be feasible. There is no difference in the second individual fitting stage for bilateral implants.

Embodiments of the present invention can significantly shorten the time-consuming fitting task without any deficit in the resulting speech performance or patient safety. On average, the scanned charge range (e.g. for MCL) in a twelve channel system can be reduced by about half in comparison to a conventional fitting procedure where each electrode channel is adjusted completely separately. For the fitting of bilaterally implanted patients, the benefit may be even greater with the scanned charge range potentially being reduced by up to 75% as compared to a conventional fitting procedure. Any behavioral and/or objective percept criteria can be used (e.g., MCL, THR, ESRT. ECAP, etc.). While increasing charge level, no overshoot will occur at any electrode contact until target level is reached. In addition, after the first common fitting stage, at least one electrode contact is known to provide auditory sensation or objective response (ESRT/ECAP), and all percept criteria are known to be above the common baseline charge level B.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

For example, a pseudo code representation of a generic embodiment might be set forth as follows:

```
Process FastChannelFitting
    deliver electrode stimulation signals to the electrode contacts at
        an initial common charge level;
    increase common charge level
        until desired common percept criteria is met
    set common baseline charge level
    for each individual electrode contact
        start common baseline charge level
        deliver fitting stimulation signal starting from the common
            baseline charge level
        increase charge level
            until individual electrode percept criteria are met
```

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant fitting system for fitting an implanted cochlear implant electrode array having a plurality of electrode contacts to the implanted patient, the system comprising:
   a normal electrode stimulation arrangement for delivering electrode stimulation signals to the electrode contacts at an initial common charge level;
   common fitting means for increasing the common charge level until a desired common percept criteria is met to establish a common baseline charge level for the electrode contacts; and
   individual fitting means for each individual electrode contact, for delivering a fitting stimulation signal to the electrode starting from the common baseline charge level and increasing the charge level until an individual electrode percept criteria is met.

2. A system according to claim 1, wherein the normal electrode stimulation arrangement uses a normal operation electrode stimulation strategy.

3. A system according to claim 2, wherein the electrode stimulation strategy is a sequential stimulation strategy.

4. A system according to claim 2, wherein the electrode stimulation strategy is a simultaneous stimulation strategy.

5. A system according to claim 2, wherein the normal electrode stimulation arrangement delivers the electrode stimulation signals in amplitude bursts.

6. A system according to claim 2, wherein the initial common charge level is an initial defined level greater than zero.

7. A system according to claim 2, wherein the initial common charge level is zero.

8. A system according to claim 2, wherein the patient is a bilateral implant patient with left and right side electrode arrays whereby all the individual electrode contacts in both arrays are fit.

9. A computer program product implemented in a tangible computer readable storage medium for fitting an implanted cochlear implant electrode array having a plurality of electrode contacts to the implanted patient, the product comprising:
   program code for using a normal electrode stimulation arrangement to deliver electrode stimulation signals to the electrode contacts at an initial common charge level;
   program code for increasing the common charge level until a desired common percept criteria is met to establish a common baseline charge level for the electrode contacts; and
   program code for each individual electrode contact, for delivering a fitting stimulation signal to the electrode starting from the common baseline charge level and increasing the charge level until an individual electrode percept criteria is met.

10. A product according to claim 9, wherein the program code for using the normal electrode stimulation arrangement includes program code for using a normal operation electrode stimulation strategy.

11. A product according to claim 10, wherein the electrode stimulation strategy is a sequential stimulation strategy.

12. A product according to claim 10, wherein the electrode stimulation strategy is a simultaneous stimulation strategy.

13. A product according to claim 9, wherein the program code for using a normal electrode stimulation arrangement delivers the electrode stimulation signals in amplitude bursts.

14. A product according to claim 9, wherein the initial common charge level is an initial defined level greater than zero.

15. A product according to claim 9, wherein the initial common charge level is zero.

16. A product according to claim 9, wherein the patient is bilateral implant patient with left and right side electrode arrays whereby all the individual electrode contacts in both arrays are fit.

17. A method of fitting an implanted cochlear implant electrode array having a plurality of electrode contacts to the implanted patient, the method comprising:
   using a normal electrode stimulation arrangement to deliver electrode stimulation signals to the electrode contacts at an initial common charge level;
   increasing the common charge level until a desired common percept criteria is met to establish a common baseline charge level for the electrode contacts; and
   for each individual electrode contact, delivering a fitting stimulation signal to the electrode starting from the common baseline charge level and increasing the charge level until an individual electrode percept criteria is met.

18. A method according to claim 17, wherein using the normal electrode stimulation arrangement includes using a normal operation electrode stimulation strategy.

19. A method according to claim 18, wherein the electrode stimulation strategy is a sequential stimulation strategy.

20. A method according to claim 18, wherein the electrode stimulation strategy is a simultaneous stimulation strategy.

21. A method according to claim 17, wherein the electrode stimulation signals are delivered in amplitude bursts.

22. A method according to claim 17, wherein the initial common charge level is an initial defined level greater than zero.

23. A method according to claim 17, wherein the initial common charge level is zero.

24. A method according to claim 17, wherein the patient is bilateral implant patient with left and right side electrode arrays whereby all the individual electrode contacts in both arrays are fit.

* * * * *